United States Patent [19]

Lewis et al.

[11] 4,414,482
[45] Nov. 8, 1983

[54] NON-RESONANT ULTRASONIC TRANSDUCER ARRAY FOR A PHASED ARRAY IMAGING SYSTEM USING $\frac{1}{4}\lambda$ PIEZO ELEMENTS

[75] Inventors: George K. Lewis, San Jose; Michael Buchin, Palo Alto, both of Calif.

[73] Assignee: Siemens Gammasonics, Inc., Des Plaines, Ill.

[21] Appl. No.: 265,623

[22] Filed: May 20, 1981

[51] Int. Cl.³ .................................... H01L 41/08
[52] U.S. Cl. ........................... 310/334; 310/336
[58] Field of Search ........................ 310/334–337; 128/660, 663; 73/632, DIG. 4, 570, 587, 603, 605, 625, 627, 628, 629, 642, 644; 367/155, 157, 162, 164, 180, 905

[56] References Cited

U.S. PATENT DOCUMENTS

| | | | |
|---|---|---|---|
| 2,589,135 | 3/1952 | Rafuse . | |
| 3,656,012 | 4/1972 | Dixon | 310/336 X |
| 4,016,530 | 4/1977 | Goll . | |
| 4,101,795 | 7/1978 | Fukumoto et al. . | |
| 4,211,948 | 7/1980 | Smith et al. . | |
| 4,211,949 | 7/1980 | Brisken et al. . | |
| 4,240,003 | 12/1980 | Larson | 310/336 X |
| 4,277,711 | 7/1981 | Hanafy | 310/336 X |
| 4,282,452 | 8/1981 | Hassler et al. . | |

*Primary Examiner*—Mark O. Budd
*Attorney, Agent, or Firm*—Karl F. Milde, Jr.

[57] ABSTRACT

A phased array transducer is disclosed for transducing ultrasound of a predetermined frequency. The transducer includes a number of piezoelectric elements, all having the same natural frequency, and having two surfaces located opposite to each other, each provided with an electrode. The distance between the two surfaces of each element is one quarter of the wavelength of the ultrasound produced by the transducer within the piezoelectric material.

12 Claims, 5 Drawing Figures

NON-RESONANT ULTRASONIC TRANSDUCER ARRAY FOR A PHASED ARRAY IMAGING SYSTEM USING ¼ λ PIEZO ELEMENTS

BACKGROUND OF THE INVENTION

1. Field of the Invention

This invention relates to a phased array transducer. In particular, this invention relates to a transducer which may be used for emitting and/or receiving ultrasound. Still more particularly, this invention relates to an ultrasonic transducer for transducing ultrasound of a predetermined frequency. The transducer is of the type which contains a large number of piezoelectric elements having all the same natural frequency. Each of these elements has a first and a second surface which are located opposite to each other, and each has a first and a second electrode which are provided on the first and the second surface, respectively. Still more particularly, the invention relates to an ultrasonic transducer for medical purposes, especially for medical ultrasound examinations.

2. Description of the Prior Art

In U.S. Pat. Nos. 4,211,948 and 4,211,949, for instance, is disclosed a phased array transducer for emitting and receiving ultrasound. The transducer contains a large number of elongated piezoelectric elements which are arranged parallel to each other. All piezoelectric elements have the same natural (mechanical) frequency. Conventionally, the piezoelectric elements contain a first and a second surface which are arranged parallel to each other. Each of these surfaces is provided with an electrode or metallic coating for connecting an electrical actuation circuit and/or an electrical evaluation circuit thereto. The depth of the piezoelectric elements is chosen such that their natural frequency is in a certain relationship to the predetermined frequency applied to the electrodes. In particular, the depth or thickness between the metallic coatings is chosen to be one half wavelength at the emission frequency. Thus, each piezoelectric element is a half wave resonator.

One of the problems associated with the prior art ultrasonic transducer resides in the fact that production becomes more difficult the thicker and narrower the individual elements must be in order to meet the requirements of frequency adjustment. In the prior art transducer arrays, the piezoelectric material tends to break during manufacture.

Another problem associated with the prior art transducer resides in the conventional resonance excitation. In a phased array arrangement the individual elements have all the same natural frequency. Since the elements are usually acoustically coupled together via a matching layer and backing, excitation of one element at resonance leads to a resonant unwanted excitation of the elements nearby. This may bring about undesired electrical and acoustic signals.

SUMMARY OF THE INVENTION

1. Objects

It is an object of this invention to provide an ultrasonic transducer for transmission and/or receiving which is easy to manufacture.

It is another object of this invention to provide an ultrasonic transducer of the type having a larger number of piezoelectric elements, which transducer has a reduced acoustic cross-talk. In other words, the individual elements shall be to a large degree acoustically uncoupled so that they are free to vibrate independently.

2. Summary

According to this invention, there is provided an improved phased array transducer for transducing ultrasound of a predetermined frequency. The transducer contains a number of piezoelectric elements all of which have the same natural frequency. Each element has a first and a second surface, which surfaces are located opposite to each other. Each element further contains first and a second electrode which are provided on the first and the second surface, respectively. The improvement resides in the following feature: The distance between the first and the second surface is chosen to be one quarter of the wavelength that ultrasound of the predetermined frequency has in the aforementioned piezoelectric element.

According to another aspect of this invention, an electrical signal is applied to each of the elements which signal contains a certain number of electrical half-waves. The frequency of the half-waves equals the predetermined frequency, and the number of half-waves should be chosen to sufficiently force the transducer but not so many as to cause loss in axial resolution. The number of half cycles should be preferably one of the numbers 3, 4, 5, 6.

Due to the mentioned distance between the surface and therefore due to the resulting value of the natural frequency, the piezoelectric elements are operated "off-resonance". Therefore, the aforementioned cross-talk is reduced. In addition, since the natural frequency of the piezoelectric elements according to the invention is higher than in elements of the prior art, the piezoelectric elements have to be thinner. Thinner piezoelectric elements can be diced much easier than thick, narrow ones.

The foregoing and other objects, features and advantages of the invention will be apparent from the following more particular description of preferred embodiments of the invention, as illustrated in the accompanying drawings.

DETAILED DESCRIPTION OF THE PREFERRED EMBODIMENTS

Figure 1:
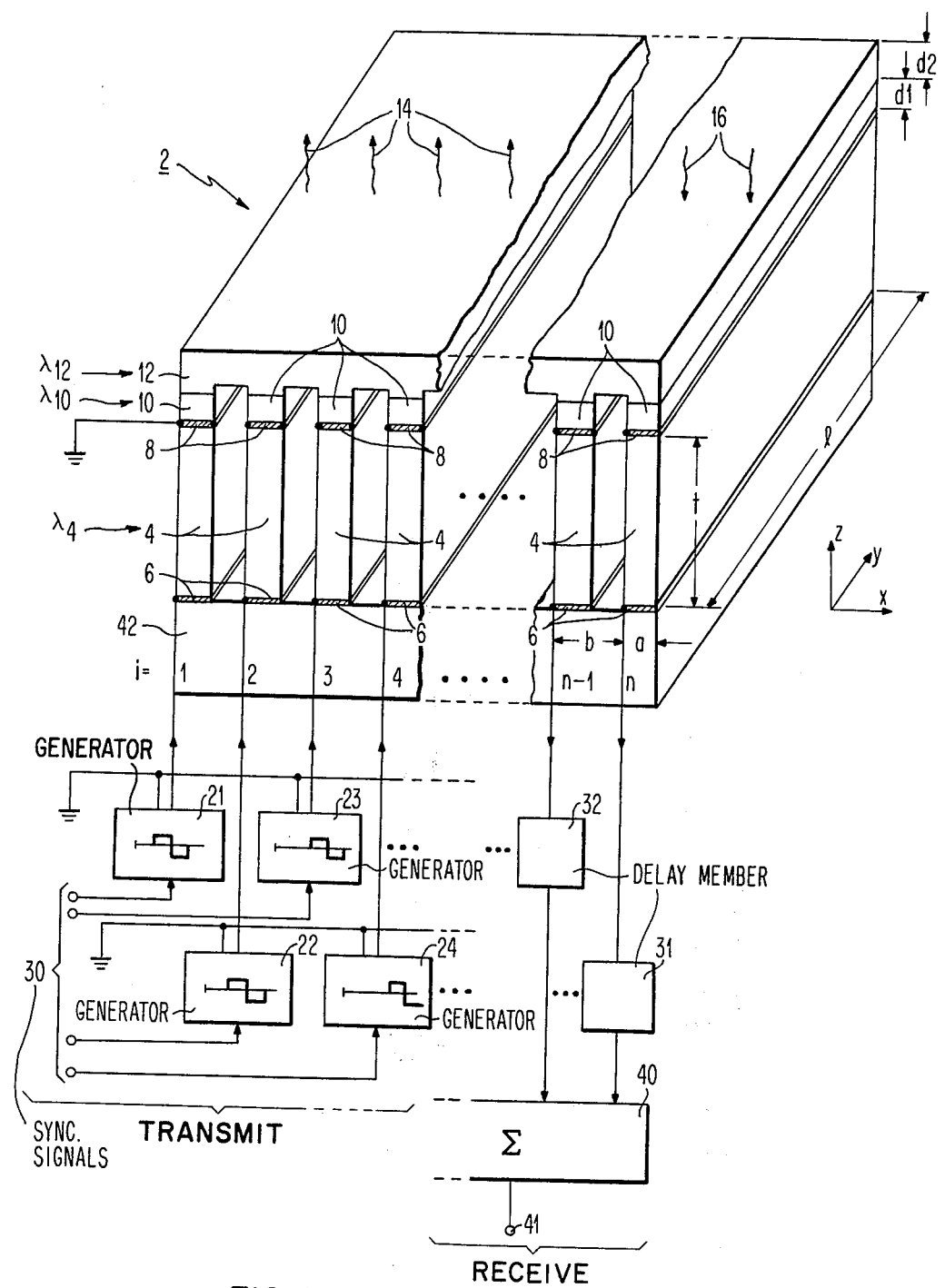
FIG. 1 is a perspective view of an ultrasonic non-resonant phased array transducer according to the invention, which transducer is provided with circuitry for transmission and for receiving of electric signals.

According to FIG. 1 a non-resonant phased array transducer for ultrasound or an ultrasonic array assembly is generally referred to by the reference numeral 2. The transducer 2 which is represented in an enlarged scale, contains a number n of elongated transducer elements 4. These elements 4 are made of a piezoelectric material, for instance a piezoelectric ceramic. The number n of elements 4 may be, for instance, 64. The elements 4 are formed as parallelepipeds. They are arranged parallel to each other. They all have the same width a, the same depth t, and the same length l. They are comparatively narrow. Grooves are provided between the individual elements 4. The distance from one side of an element 4 to the corresponding side of the next element 4 is designated as b. The grooves to some extent avoid acoustic cross-coupling. They may be filled with acoustically non-conducting material (not shown).

Each element 4 has a first and a second surface which are located opposite and parallel to each other. On the lower surfaces are provided first metallic coatings or electrodes 6, and on the upper surfaces are provided second metallic coatings or electrodes 8. The second electrodes 8 are jointly connected to ground, whereas the first electrodes 6 are provided with individual connection leads. Connected to these leads is a transmission circuitry, as illustrated in the left part of FIG. 1, and also a receiving circuitry, as illustrated in the right part of FIG. 1.

Important is that the value of the natural frequencies of the individual piezoelectric elements 4 is selected higher than in currently manufactured transducer arrays. The natural frequency is dependent on the type of piezoelectric material which is used and on the distance t between the electrodes 6 and 8. In particular, the thickness or distance t between the two surfaces covered by the electrodes 6 and 8, respectively, is chosen to be one quarter of the wavelength $\lambda_4$ which ultrasound of the predetermined ultrasound frequency (emission frequency) has in the element 4. Therefore, the elements 4 may be termed as "quarter wave resonators".

The upper or second electrodes 8 are firmly connected to impedance matching layers or elements 10. These matching elements 10, in turn, are jointly covered by a continuous matching layer or plate 12. The matching elements 10 and the matching plate 12 serve to match the energy transfer of an outgoing ultrasound wave 14 to the environment which is to be investigated and/or to match the energy transfer of an incoming ultrasound wave 16 to the piezoelectric elements 4 applied. The environment to be examined may be the body of a patient. The thickness $d_1$ of each of the matching elements 10 preferably is approximately one eighth of the wavelength $\lambda_{10}$ which ultrasound of the predetermined ultrasound frequency (emmission frequency) has in the respective matching element 10. Correspondingly, the thickness $d_2$ of the matching plate 12 preferably is approximately one eighth of the wavelenth $\lambda_{12}$ which ultrasound of the predetermined ultrasound frequency (emission frequency) has in the matching plate 12. The lower electrode 6 is firmly attached to a rigid low acoustic impedance highly attenuating backing support 42.

The transmission circuitry contains a number n of individual generators of which only four generators 21, 22, 23 and 24 are illustrated in FIG. 1. These generators 21-24 are provided for applying an electrical signal to the electrodes 6, 8. Thereby the elements 4 are caused to vibrate. As will be illustrated in FIGS. 2-5, the electrical signals each contain a predetermined number of electrical half-waves whose frequency is equal to the predetermined ultrasound frequency (emission frequency) and whose number is between 3 and 6.

As can be seen from the time diagrams in the generator blocks 21-24, the electrical signals are time-displaced with respect to each other. In order to achieve this, the generators 21-24 are fed by synchronizing signals which are applied to a plurality of inputs 30. The individual generators 21-24 generate time delayed output signals which are spaced from each other. Alternatingly, the transmission circuitry may comprise a single generator which generates a train of half-waves. The number of half-waves is predetermined. The circuitry may also comprise a number n of delay members associated with respective ones of the elements 4 for delaying the train of half-waves. In the array of delay members, the delay time increases. This embodiment is not shown in FIG. 1.

As can be seen on the right side of FIG. 1, the receiving circuitry contains a number n of delay members. Only the two delay members 31 and 32 are illustrated. The delay members 31, 32, ... delay the received input signals. The delay times are different from each other. The output signals of the delay members 31, 32, ... are applied to a summing element 40, the output 41 of which delivers an output signal which may be used for imaging purposes.

Figure 2:
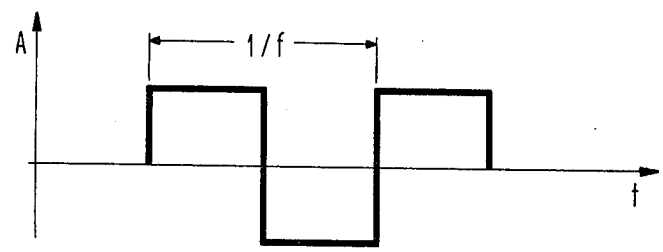
FIG. 2 is a time diagram of an electrical signal containing three square half-waves, which signal is applied to an element of the transducer according to FIG. 1.
Figure 3:
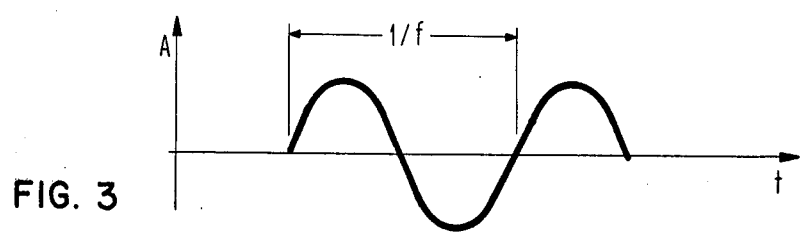
FIG. 3 is a time diagram of an electrical signal containing three sinusoidal half-waves.

It has been mentioned before that the number of half-waves should be limited. Preferably, the number of half-waves should be one of the numbers 3 to 6. In a preferred embodiment, as illustrated in FIGS. 2 and 3, the number of half-waves is 3. In FIG. 2 square half-waves are used, whereas in FIG. 3 sinusoidal half-waves are applied.

Figure 4:
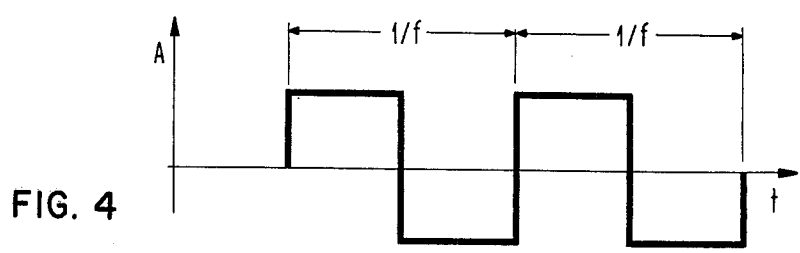
FIG. 4 is a time diagram of an electrical signal containing four square half-waves.
Figure 5:
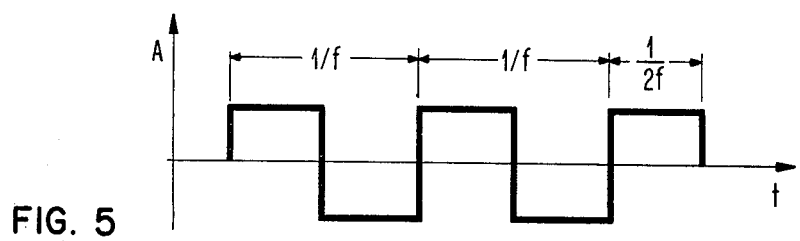
FIG. 5 is a time diagram of an electrical signal containing five square half-waves for application to an element of the transducer according to FIG. 1.

In FIG. 4 is illustrated that four square half-waves can be used, and in FIG. 5 is shown that even five square half-waves may be applied. It should also be mentioned that any combination may be used.

An example with respect to the dimensions of a prior art transducer and of a transducer according to the invention will now be given. It is, however, understood that the invention is by no way restricted to the precise values mentioned below.

First a typical prior art transducer is considered. It is assumed that the prior art transducer is designed for an ultrasound frequency f=2.25MHz. It is also assumed that n=64 elements 4 are provided which are in the form of elongated parallelepiped blocks. For each of the n elements 4 the same commercially available piezoelectric ceramic is selected. Each of these n elements has a depth t=36 mils and a width a=8 mils (1 mil=0.001 inch). The depth t=36 mils corresponds to one half of the wavelength $\lambda_4$ which ultrasound of 2.25 MHz has in the selected ceramic, that is t=$\lambda_4$/2. Due to the chosen dimensions of the selected ceramic, the mechanical natural frequency is 2.25 MHz. When the conventional shock excitation is used, the elements 4 will vibrate parallel to the z axis with a frequency f=2.25 MHz, that is in resonance. Both matching layers 10 and 12 have a thickness d1 and d2 of approximately d1=9 mils and d2=10 mils. The thickness d1 and d2 corresponds in both cases to one quarter of the wavelength $\lambda_{10}$ and $\lambda_{12}$, respectively, which ultrasound of 2.25 MHz has in the selected matching layers 10 and 12. The distance b from element to element equals b=$\lambda_b$/2, wherein $\lambda_b$ is the wavelength of ultrasound having the frequency f in the body of a patient.

It is now assumed that a transducer according to the invention is designed for the same ultrasound frequency f=2.25 MHz. The same piezoelectric ceramic material will be used as in the previous example. While the width a and the length l of each element 4 stay the same as above, the depth t of each element 4 is changed. The depth t is now half the value it has been previously, that is now t=18 mils. Smaller elements having a depth of t=18 mils are easier to produce than thicker ones having a depth of t=36 mils. The depth t corresponds now to one quarter of the wavelength $\lambda_4$ which ultrasound of 2.25 MHz has in the ceramic, that is $$t = \lambda_4/4.$$

It will be noted that due to the decrease of the depth t of the element 4 to half its former value, the resonance frequency $f_r$ of the ceramic between the electrodes doubles. The resonance frequency is now $f_r=4.50$ MHz. If the conventional shock excitation were used, here again the elements 4 would vibrate with a frequency of 4.50 MHz along the z axis. Yet, the conventional shock excitation is no longer applied. Instead, according to the invention, the mentioned half-cycle excitation with half-cycles corresponding to the frequency f=2.25 MHz is used. Thus, due to the forced excitation, each element 4 is clearly operated off resonance. The mechanical z extension of each element 4 will follow the electrical amplitude during the half-cycle excitation, that is each element 4 will respond with vibrations having the frequency f=2.25 MHz. Therefore, the transducer according to the invention may be termed "quarter wave resonator". Since the excitation is not performed with the resonance frequency of 4.50 MHz, unwanted resonance coupling from one element 4 which is just excited to another element 4 (via air or the matching layers) does not occur.

It should be mentioned that the thickness of the two matching layers 10, 12 may be $d_1=4.5$ mil and $d_2=5$ mil, that is half the former size.

The ultrasonic transducer array illustrated in FIG. 1 is easier to manufacture than presently known arrays.

This is true because for a given ultrasound frequency the thickness t is smaller than in presently known designs. Therefore, the ratio t/a is comparatively small. Consequently, the elements 4 are less likely to break during the dicing process. Since a non-resonance frequency is chosen, cross-coupling from one element 4 to the next can widely be excluded. The off-resonance operation therefore results in a reduced acoustic crosstalk. Since half the depth dimensions may be used as compared to prior art arrays, each element 4 had twice the capacitance of a prior art element. This means that its electrical impedance is less than the former value. This leads to a better electrical matching to the electrical circuitry, which in turn improves the sensitivity of each individual element 4.

Another advantage resides in the fact that a controlled response is possible since preferably only 3, 4 or 5 half cycles are applied in emission. In other words, the electrical signal controls the behaviour of the respective element, not the mechanical status of the element itself. Therefore, inhomogeneities contained in the element will not be exhibited in the output signal.

In investigations of a transducer according to the invention, an interesting effect was observed. The ultrasound signal emitted from the transducer retains its wave-form if one goes off-axis. This is in contrast to prior art transducers where the signal becomes longer in time if the signal is observed off-axis.

While the forms of the non-resonant ultrasonic transducer array for a phased array imaging system herein described constitute preferred embodiments of the invention, it is to be understood that the invention is not limited to these precise forms of assembly, and that a variety of changes may be made therein without departing from the scope of the invention.

What is claimed is:

1. In a phased array transducer for transducing ultrasound of a predetermined frequency, comprising
   (a) a plurality of piezoelectric elements having all the same natural frequency, each of said elements having a first and a second surface which are located opposite to each other, and
   (b) a first and a second electrode provided on said first and said second surface, respectively, of each of said elements, the improvement wherein a distance between said first and second surface is one quarter of the wavelength that ultrasound of said predetermined frequency has in said element between said electrodes.

2. The improvement according to claim 1, further comprising means for applying an electrical signal to said electrodes and for thereby causing said elements to vibrate, whereby said electrical signal contains a plurality of electrical half-waves whose frequency is equal to said predetermined frequency and whose number is between 3 and 6.

3. The improvement according to claim 2, wherein said number of half-waves is selected from the numbers 3 to 6.

4. The improvement according to claim 3, wherein said number is 3.

5. The improvement according to claim 1, wherein said first and second surfaces are parallel to each other.

6. The improvement according to claim 1, wherein said half-waves are square half-waves.

7. The improvement according to claim 1, wherein said half-waves are sinusoidal half-waves.

8. The improvement according to claim 1, wherein said elements are arranged parallel to each other and connected to a matching plate.

9. The improvement according to claim 8, wherein the thickness of said matching plate is approximately one-eighth of the wavelength which ultrasound of said predetermined frequency has in said matching plate.

10. The improvement according to claim 8, wherein additional matching elements are provided between said respective elements and said matching plate.

11. The improvement according to claim 10, wherein the thickness of each of said matching elements is approximately one-eighth of the wavelength which ultrasound of said predetermined frequency has in said matching elements.

12. The improvement according to claim 2, wherein said means for applying said electrical signal comprises a plurality of generators for generating time-displaced trains of half-waves for said elements.

* * * * *